United States Patent [19]

Grassberger et al.

[11] 4,382,951

[45] May 10, 1983

[54] BENZOPYRANE AND BENZOTHIOPYRANE DERIVATIVES USEFUL AS ANTI-MYCOTIC AGENTS

[75] Inventors: Maximilian Grassberger, Vienna; Gabor Petranyi, Schwechat, both of Austria

[73] Assignee: Sandoz Ltd., Basel, Switzerland

[21] Appl. No.: 329,171

[22] Filed: Dec. 10, 1981

[30] Foreign Application Priority Data

Dec. 15, 1980 [CH] Switzerland ............................ 9232/80

[51] Int. Cl.$^3$ ...................... A61K 31/35; A61K 31/38; C07D 311/04; C07D 335/06
[52] U.S. Cl. ..................................... 424/275; 424/283; 549/23; 549/60; 549/407
[58] Field of Search ............................ 549/23, 60, 407; 424/275, 283

[56] References Cited

U.S. PATENT DOCUMENTS

3,419,560  12/1968  Bernstein et al. .................. 549/23 X
4,282,251  8/1981   Berney ................................. 424/316
4,321,270  3/1982   Sundeen ........................... 549/407 X

FOREIGN PATENT DOCUMENTS

896  3/1979  European Pat. Off. .

Primary Examiner—Richard Raymond
Attorney, Agent, or Firm—Gerald D. Sharkin; Richard E. Vila; Frederick H. Weinfeldt

[57] ABSTRACT

Benzopyrane and benzothiopyrane derivatives which possess pharmaceutical in particular anti-mycotic activity.

19 Claims, No Drawings

BENZOPYRANE AND BENZOTHIOPYRANE DERIVATIVES USEFUL AS ANTI-MYCOTIC AGENTS

The present invention concerns new organic compounds, in particular benzopyrane and benzothiopyrane derivatives, processes for their production and their use.

All formulae referred to in the specification and claims are as shown hereinafter on the formula sheets and reaction schemes.

The invention concerns more particularly a compound of formula I wherein,

X represents oxygen or sulphur, each $R_1$ represents independently hydrogen or methyl, $R_3$ and $R_4$ represent independently hydrogen, halogen, lower alkyl or lower alkoxy, $R_2$ and $R_5$ represent independently hydrogen, halogen, lower alkyl, lower alkoxy or a group of formula II, and $R_6$ represents hydrogen, lower alkyl or a group of formula II, whereby one and only one group of formula II is always present as $R_2$, $R_5$ or $R_6$;

$R_7$ and $R_8$ represent independently hydrogen or lower alkyl, $R_9$ represents lower alkyl and $R_{11}$ represents a group of formula IIa, IIb, IIc or IId, wherein $R_{12}$ represents hydrogen, halogen, trifluoromethyl, lower alkyl or lower alkoxy, at least one of $R_{13}$, $R_{14}$ and $R_{15}$ represents alkyl and the others represent hydrogen or alkyl, or $R_{14}$ together with either $R_{13}$ or $R_{15}$ forms a $C_{3-6}$methylene bridge and $R_{16}$ represents lower alkyl, lower alkenyl or α-hydroxy lower alkyl;

or an acid addition salt thereof.

According to the invention, the compounds of formula I may be obtained by (a) reacting a compound of formula III, wherein $R_2^I$ and $R_5^I$ represent independently hydrogen, halogen, lower alkyl, lower alkoxy or a group of formula IIe and $R_6^I$ represents hydrogen, lower alkyl or a group of formula IIe, whereby one and only one group of formula IIe is always present as $R_2^I$, $R_5^I$ or $R_6^I$ and X, $R_1$, $R_3$, $R_4$, $R_7$, $R_8$ and $R_9$ are as defined above, with a compound of formula IV, wherein $R_{11}$ is as defined above and A represents a leaving group, or (b) reacting a compound of formula IIIa, wherein $R_2^{II}$ and $R_5^{II}$ represent independently hydrogen, halogen, lower alkyl, lower alkoxy or a group of formula IIf and $R_6^{II}$ represents hydrogen, lower alkyl or a group of formula IIf, whereby one and only one group of formula IIf is always present as $R_2^{II}$, $R_5^{II}$ or $R_6^{II}$ and X, $R_1$, $R_3$, $R_4$, $R_7$, $R_8$ and A are as defined above with a compound of formula IVa, wherein $R_9$ and $R_{11}$ are as defined above, (c) alkylating a compound of formula V, wherein $R_2^{III}$ and $R_5^{III}$ represent independently hydrogen, halogen, lower alkyl, lower alkoxy or a group of formula IIg and $R_6^{III}$ represents hydrogen, lower alkyl or a group of formula IIg whereby one and only one group of formula IIg is always present as $R_2^{III}$, $R_5^{III}$ or $R_6^{III}$ and X, $R_1$, $R_3$, $R_4$, $R_7$, $R_8$ and $R_{11}$ are as defined above, or (d) to produce a compound of formula I wherein $R_7$ and $R_8$ are hydrogen reacting a compound of formula VI wherein $R_2^{IV}$ and $R_5^{IV}$ represent independently hydrogen, halogen, lower alkyl, lower alkoxy or formyl and $R_6^{IV}$ represents hydrogen, lower alkyl or formyl, whereby one and only one formyl is always present as $R_2^{IV}$, $R_5^{IV}$ or $R_6^{IV}$, and X, $R_1$, $R_3$ and $R_4$ are as defined above, with a compound of formula IVa, wherein $R_9$ and $R_{11}$ are as defined above.

Processes (a) and (b) can be carried out in conventional manner, for example in a solvent, inert under the reaction conditions, such as an optionally aqueous alcohol, a halogenated hydrocarbon such as dichloromethane, an aromatic hydrocarbon such as benzene or toluene, a cyclic ether, such as dioxane or a carboxylic acid dialkylamide, such as dimethylformamide and at temperatures between room temperature (which is preferred) and the boiling point of the reaction mixture. Depending on the nature of the leaving group A, which can for example be iodine or preferably chlorine or bromine, or an organic sulphonyloxy group having 1 to 10 carbon atoms, e.g. alkylsulphonyloxy, preferably having 1 to 4 carbon atoms such as mesyloxy, or alkylphenylsulphonyloxy preferably having 7 to 10 carbon atoms such as tosyloxy, the reaction is conveniently carried out when appropriate in the presence of an acid binding agent, e.g. an alkali or alkaline earth metal hydroxide or carbonate such as sodium carbonate.

Process (c) can be carried out in accordance with conventional alkylating conditions, e.g. by direct alkylation with an alkylating agent such as an alkyl halogenide or a sulphuric acid ester, or alkylation with an aldehyde and subsequent or simultaneous reduction (reductive alkylation). Reductive alkylation can for example be carried out by dissolving or suspending a compound of formula V in a solvent inert under the reaction conditions such as a lower alcohol, e.g. methanol, adding the appropriate aldehyde and reacting, preferably at raised temperature, especially at the boiling point of the reaction mixture. Reduction is then carried out in conventional manner, e.g. using a complexed hydride such as $NaBH_4$ or $NaCNBH_3$ whereby solvent and temperature will vary according to the method chosen. Direct reductive alkylation can be achieved using e.g. formic acid as both solvent and reducing agent at the boiling point of the reaction mixture.

Process (d) can be carried out under conditions e.g. as described above for reductive alkylation.

The compounds of formula I may be converted in conventional manner into their acid addition salts and vice versa. Suitable acid addition salts are e.g. hydrochloride, hydrogen fumarate or naphthalene-1,5-disulphonate.

The compounds of the formula I and their intermediates can be obtained in the form of isomeric mixtures of the various cis/trans isomers which can be separated according to established methods. Alternatively, isomers of the compounds can be obtained by using the appropriate isomer of the starting material.

Any lower alkyl or lower alkoxy radical has preferably 1 to 4 carbon atoms, especially 2 or 1 carbon atoms. Unless otherwise stated alkyl moieties preferably have 1 to 10 carbon atoms especially 1 to 5 carbon atoms. Any lower alkenyl radical has preferably 3 to 6 carbon atoms, especially 3 or 4, e.g. allyl. Halogen stands for fluorine, chlorine or bromine.

The starting materials of formula III are in part new and can be prepared by reacting in conventional manner a compound of formula VIII, wherein X, $R_1$, $R_3$ and $R_4$ are as defined above and $R_2^V$ and $R_5^V$ represent independently hydrogen, halogen, lower alkyl, lower alkoxy or a group of formula IIh, $R_6^V$ represents hydrogen, lower alkyl or a group of formula IIh, whereby one and only one group of formula IIh is always present as $R_2^V$, $R_5^V$ and $R_6^V$, and Hal represents halogen, with a compound of formula IX, wherein $R_9$ is as defined above.

Compounds of formula IV, wherein $R_{11}$ represents a compound of formula IId as defined above (compounds IVb) are partly new and can be prepared, e.g. according to reaction scheme 1.

Compounds of formula V are partly new and can be prepared in conventional manner e.g. by reacting a compound of formula XV, wherein X, $R_1$, $R_3$ and $R_4$ are as defined above, and $R_2^{VI}$ and $R_5^{VI}$ represent independently hydrogen, halogen, lower alkyl, lower alkoxy or a group of formula IIi and $R_6^{VI}$ represents hydrogen, lower alkyl or a group of formula IIi, whereby one and only one group of formula IIi is always present as $R_2^{VI}$, $R_5^{VI}$ or $R_6^{VI}$, with a compound of formula XVI, wherein $R_{11}$ is as defined above to give a corresponding compound of formula XVII, wherein $R_2^{VII}$ and $R_5^{VII}$ represent independently hydrogen, halogen, lower alkyl, lower alkoxy or a group of formula IIj and $R_6^{VII}$ represents hydrogen, lower alkyl or a group of formula IIj, whereby one and only one group of formula IIj is always present as $R_2^{VII}$, $R_5^{VII}$ or $R_6^{VII}$; which is then reduced e.g. as described under process (c).

The compounds of formula VIII wherein $R_1$ represents methyl can be prepared e.g. according to reaction scheme 2.

These new intermediates also form part of the invention.

The remaining intermediate compounds are either known or can be prepared according to known methods or as hereinbefore described.

The compounds of formula I exhibit chemotherapeutic activity. In particular, they exhibit anti-mycotic activity, as indicated in vitro in various families and types of mycetes, including Trichophyton spp, Aspergillus spp, Microsporum spp, *Sporotrychium schenkii* and Candida spp at concentrations of, for example 0.1 to 100 μg/ml, and in vivo in the experimental skin mycosis model in guinea pigs. In this model, guinea pigs are infected by sub-cutaneous applications of Trichophyton quinckeanum. The test substance is administered daily for 7 days beginning 24 hours after the infection either on local application by rubbing the test substance (taken up in polyethylene glycol) on the skin surface, or per-orally or sub-cutaneously, the test substance being administered as a suspension. The activity is shown on local application at concentrations of for example 0.1 to 2%. The oral activity is shown in vivo in the quinea-pig-Trichophytosis model at dosages of, for example, 10 to 300 mg/kg.

The compounds may therefore be used as anti-mycotic agents. For this use, the effective dosage will, of course, vary depending on the particular compound employed, the mode of administration and the treatment desired. However, in general, satisfactory results can be obtained when the compounds are administered at a daily dosage of from about 4 to 30 mg/kg of animal body weight, suitably given in divided doses two to four times daily. For most large mammals, the total daily dosage is from about 300 to 2000 mg and dosage forms suitable for internal administration comprise about 75 to 1000 mg of the compound in admixture with a solid or liquid chemotherapeutical carrier or diluent.

The compounds of formula I may be administered in similar manner to known standards for use in such indications e.g. Griseofulvin.

The suitable daily dosage for a particular compound will depend on a number of factors such as its relative potency of activity. It has, for example, been determined in the guinea-pig-Trichophytosis model that two of the preferred compounds of this invention, namely trans-N-(2H-1-benzopyran-4-yl-methyl)-N-methyl-6,6-dimethylhept-2-en-4-ynyl-1-amine and trans-N-(6-fluoro-2H-1-benzopyran-4-yl-methyl)-N-methyl-6,6-dimethylhept-2-en-4-ynyl-1-amine have a curative dose (i.e. the dose sufficient to cure guinea pigs infected with *Trichophyton mentagrophytes* var. quinckeanum Δ158 of all mycological symptoms) of $9 \times 12$ mg/kg/day as compared to $9 \times 70$ mg/kg/day for Griseofulvin. It is therefore indicated that these compounds may be administered at similar or lower dosages than conventionally employed for Griseofulvin.

The compounds may be used in free base form or in the form of chemotherapeutically acceptable acid addition salts. Such salt forms exhibit the same order of activity as the free base forms. Suitable such salt forms are e.g. hydrochloride, hydrogen fumarate or naphthalene-1,5-disulphonate.

The compounds may be admixed with conventional chemotherapeutically acceptable diluents and carriers, and, optionally, other excipients and administered in such forms as tablets or capsules. The compounds may alternatively be administered topically in such conventional forms as ointments or creams or parenterally. The concentrations of the active substance will of course vary depending on the compound employed, the treatment desired and the nature of the form etc. In general, however, satisfactory results are obtained e.g. in topical application forms at concentrations of from 0.05 to 5, in particular 0.1 to 1 wt %.

Such compositions also form part of the invention.

Preferred meanings for the substituents are as follows:

for $R_1$ both hydrogen or both methyl;
for $R_2$ and $R_5$ independently hydrogen or halogen, in particular fluorine or chlorine;
for $R_6$ a group of formula II;
for $R_3$ and $R_4$ independently hydrogen, halogen or lower alkyl in particular hydrogen, chlorine or methyl;
for $R_7$ and $R_8$ hydrogen;
for $R_9$ methyl;
for $R_{11}$
  =IIa, wherein $R_{12}$ is preferably hydrogen,
  =IIb, wherein $R_{12}$ is preferably hydrogen,
  =IIc, wherein $R_{13}$ and $R_{14}$ are preferably hydrogen and $R_{15}$ is preferably lower alkyl e.g. t.butyl, or
  =IId, wherein $R_{16}$ is preferably lower alkyl e.g. t.butyl,
  particularly preferred hereby being $R_{11}$=IId;
and for X oxygen;
and combinations of these.

The double bond between $R_{11}$ and the nitrogen atom preferably has the trans-configuration.

A particular compound group comprises such of formula I, wherein
X represents oxygen,
$R_1$, $R_3$ and $R_4$ are as defined above, $R_2$ and $R_5$ represent hydrogen, halogen, lower alkyl, or lower alkoxy, $R_6$ represents a group of formula II and $R_7$, $R_8$, $R_9$, $R_{11}$, $R_{12}$, $R_{13}$, $R_{14}$, $R_{15}$ and $R_{16}$ are as defined above;

Two particularly preferred single compounds are:
trans-N-(6-fluoro-2H-1-benzopyran-4-yl-methyl)-N-methyl-6,6-dimethylhept-2-en-4-ynyl-1-amine; and
trans-N-(2H-1-benzopyran-4-yl-methyl)-N-methyl-6,6-dimethylhept-2-en-4-ynyl-1-amine and their hydrochlorides.

The following Examples illustrate the invention whereby all temperatures are in degrees centigrade.

EXAMPLE 1

Trans,trans-N-(6-chloro-2H-1-benzopyran-4-yl-methyl)-N-methyl-6,6-dimethylhepta-2,4-dienyl-1-amine (Process a) (Compound No.1)

1.2 ml of triethylamine are added dropwise to 0.56 g of trans,trans-6,6-dimethylhepta-2,4-dien-1-ol and 0.5 g of methanesulphochloride in 15 ml of dichloromethane at $-5°$ to $2°$ and the mixture stirred for 30 minutes at room temperature. 0.92 g of N-(6-chloro-2H-1-benzopyran-4-yl-methyl)methylamine dissolved in 10 ml of dichloromethane are then added dropwise and the mixture stirred for 1½ hours at room temperature. The resulting reaction mixture is poured onto ice-water and the organic phase separated, washed with saturated aqueous NaCl, dried over $MgSO_4$ and concentrated by evaporation. The residue is chromatographed on kieselgel (eluant toluene/ethylacetate; 9/1).

EXAMPLE 2

Trans-N-(2H-1-benzopyran-4-yl-methyl)-N-methyl-cinnamylamine (Process b) (Compound No.2)

1.15 g of trans-N-cinnamyl-methylamine in 20 ml of dimethylformamide are slowly added dropwise with stirring to 1.4 g of 4-chloromethyl-2H-1-benzopyrane and 0.8 g of sodium carbonate in 40 ml dimethylformamide. Stirring is continued for 24 hours at room temperature, the resulting mixture evaporated under vacuum and the residue taken up in ethylacetate/water. The organic phase is separated, washed with 1% tartaric acid, saturated $NaHCO_3$ and saturated NaCl, dried over $MgSO_4$ and concentrated by evaporation. After purification by chromatography on kieselgel (eluant toluene/ethylacetate 10/1) the title compound is obtained.

EXAMPLE 3

Trans-N-(2H-1-benzopyran-8-yl-methyl)-N-methyl-6,6-dimethylhept-2-en-4-ynyl-1-amine (Process d) (Compound No.3)

370 mg of trans-N-(6,6-dimethylhept-2-en-4-ynyl)-methylamine in 20 ml of methanol are reacted with 0.3 ml of 8 N ethanolic hydrochloric acid. 100 mg of 8-formyl-2H-1-benzopyrane in 10 ml of methanol and 22 mg of $NaCNBH_3$ are then added and the mixture stirred for 12 hours at room temperature. The reaction mixture is then concentrated on a rotary evaporator, the residue taken up in ethylacetate and 0.1 N KOH and the organic phase separated off. This is then washed with aqueous $NaHCO_3$ and saturated aqueous NaCl, dried over $MgSO_4$ and concentrated by evaporation. After purification by chromatography on kieselgel (eluant toluent/ethylacetate 4/1) the title compound is obtained.

Analogously to Examples 1 to 3 or as otherwise described hereinbefore, the following compounds of formula I' and I" can be obtained.

TABLE 1

(formula I')

| Cmpd. No. | $R_2$ | $R_3$ | $R_4$ | $R_5$ | $R_{11}$ | Isomer |
|---|---|---|---|---|---|---|
| 4 | Cl | H | H | H | $-C_6H_5$ | trans |
| 5 | H | H | Cl | H | $-C_6H_5$ | trans |
| 6 | H | H | $CH_3$ | H | $-C_6H_5$ | trans |
| 7 | Cl | H | Cl | H | $-C_6H_5$ | trans |
| 8 | H | H | Cl | H | $-C\equiv C-C(CH_3)_3$ | trans |
| 9 | H | H | Cl | H | $-CH=CH-C(CH_3)_3$ | trans |
| 10 | H | H | H | F | $-C\equiv C-C(CH_3)_3$ | cis |
| 11 | H | H | H | F | $-C\equiv C-C(CH_3)_3$ | trans |
| 12 | H | H | H | F | $-C\equiv C-C(CH_3)_3$ | trans |
| 13 | H | H | H | F | $-C_6H_5$ | trans |
| 14 | H | F | H | H | $-C\equiv C-C(CH_3)_3$ | cis |
| 15 | H | F | H | H | $-C_6H_5$ | trans |
| 16 | H | F | H | H | $-C\equiv C-C(CH_3)_3$ | trans |
| 17 | F | H | H | H | $-C\equiv C-C(CH_3)_3$ | cis |
| 18 | F | H | H | H | $-C\equiv C-C(CH_3)_3$ | trans |
| 19 | F | H | H | H | $-C_6H_5$ | trans |
| 20 | H | H | F | H | $-C_6H_5$ | trans |
| 21 | H | H | F | H | $-C\equiv C-C(CH_3)_3$ | trans |
| 22 | H | H | F | H | $-C\equiv C-C(CH_3)_3$ | cis |
| 23 | H | Cl | H | Cl | $-C_6H_5$ | trans |
| 24 | H | H | H | Cl | $-C_6H_5$ | trans |
| 25 | H | Cl | H | H | $-C_6H_5$ | trans |

TABLE 2

(Formula I")

| Cmpd. No. | $R_2$ | $R_3$ | $R_4$ | $R_5$ | $R_{11}$ | Isomer |
|---|---|---|---|---|---|---|
| 26 | H | H | H | H | $-C\equiv C-C(CH_3)_3$ | cis |
| 27 | H | H | H | H | $-C\equiv C-C(CH_3)_3$ | trans |
| 28 | H | H | H | H | $-C_6H_5$ | trans |

Proceeding analogously to Examples 1 to 3 or as otherwise described hereinbefore, the following compound can also be obtained trans-N-(2H-1-benzothiopyran-4-yl-methyl)-N-methyl-cinnamylamino (Compound 29).

All of the compounds 1 to 29 are oils characterised by the following NMR data:

| Cmpd. No. | H-NMR-Data (CDCl$_3$), [ppm] |
|---|---|
| 1,9 | 7,44 (d, J=3 Hz, 1H); 7,07 (dd, J$_1$=3 Hz, J$_2$=10 Hz, 1H); 6,72 (d, J=10 Hz, 1H); 5,5–6,35 (m,5H); 4,70–4,83 (m,2H); 3,13–3,24 (m,2H); 3,05 (d, J=7 Hz, 2H); 2,20 (s,3H); 1,02 (s,9H). |
| 2 | 6,7–7,5 (m,9H); 6,5 (d, J=16 Hz, 1H); 6,2 (dt, J$_1$=16 Hz, J$_2$=6 Hz, 1H; 5,8 (m,1H); 4,68 (m,2H); 3,22 (m,2H); 3,13 (d, J=6 Hz, 2H); 2,2 (s,3H). |
| 3 | 6,66–7,16 (m,3H); 6,33 (d, J=10 Hz, 1H); 5,2–6,14 (m,3H); 4,6–4,8 (m,2H); 3,42 (s,2H); 3,03 (d, J=6 Hz, 2H); 2,17 (s, 3H); 1,20 (s,9H). |
| 4 | 7,1–7,6 (m,7H); 6,84 (t, J=8 Hz, 1H); 6,58 (d, J=15 Hz, 1H); 6,28 (dt, J$_1$=15 Hz, J$_2$=6 Hz, 1H); 5,82 (m,1H); 4,9 (m,2H); 3,3 (m,2H); 3,22 (d, J=6 Hz, 2H); 2,28 (s,3H). |
| 5 | 7,0–7,6 (m,8H); 6,62 (d, J=17 Hz, 1H); 6,32 (dt, J$_1$=17 Hz, J$_2$=6 Hz, 1H); 5,82 (m,1H); 4,8 (m,2H); 3,15–3,30 (m,4H); 2,28 (s,3H). |
| 6 | 6,7–7,5 (m,8H); 6,65 (d, J=17 Hz, 1H); 6,32 (dt, J$_1$=17 Hz, J$_2$=6 Hz, 1H); 5.80 (m,1H); 4,76 (m,2H); 3,15–3,35 (m, 4H); 2,30 (s,3H); 2,27 (s,3H). |
| 7 | 6,7–7,6 (m,7H); 6,56 (d, J=16 Hz, 1H); 6,26 (dt, J$_1$=16 Hz, J$_2$=6 Hz, 1H); 5,82 (m,1H); 4,86 (m,2H); 3,1–3,4 (m, 4H); 2,24 (s,3H). |
| 8 | 7,4 (d, J=2 Hz, 1H); 7,05 (d, J$_1$=9 Hz, J$_2$=2 Hz, 1H); 6,70 (d, J=9 Hz, 1H); 6,10 (dt, J$_1$=15 Hz, J$_2$=6 Hz, 1H); 5,5–5,75 (m,2H); 4,77 (m,2H); 3,20 (s, breit, 2H); 3,05 (d, J=6 Hz, 2H); 2,21 (s,3H); 1,24 (s,9H). |
| 10 | 6,98–7,28 (m,1H); 6,54–6,70 (m,2H); 5,84–6,15 (m,2H); |

| Cmpd. No. | H-NMR-Data (CDCl$_3$), [ppm] |
|---|---|
| | 5,63 (d, J=12 Hz, 1H); 4,63–4,75 (m,2H); 3,40–3,50 (m, 2H); 3,34 (dd, J$_1$=2 Hz, J$_2$=7 Hz, 2H); 2,28 (s,3H); 1,28 (s, 9H). |
| 11 | 6,73–7,50 (m,4H); 6,11 (dt, J$_1$=7 Hz, J$_2$=17 Hz, 1H); 5,5–5,75 (m,2H); 4,70–4,84 (m,2H); 3,17–3,28 (m,2H); 3,06 (dd, J$_1$=1,5 Hz, J$_2$=7 Hz, 2H); 2,21 (s,3H); 1,23 (s,9H). |
| 12 | 6,45–7,14 (m,3H); 6,04 (dt, J$_1$=6 Hz, J$_2$=16 Hz, 1H); 5,80–5,94 (m,1H); 5,57 (d, J=16 Hz, 1H); 4,54–4,68 (m,2H); 3,20–3,33 (m,2H); 3,04 (d, J=6 Hz, 2H); 2,19 (s,3H); 1,21 (s,9H). |
| 13 | 6,40–7,45 (m,9H); 6,23 (dt, J$_1$=6 Hz, J$_2$=16 Hz, 1H); 5,82–6,00 (m,1H); 4,58–4,70 (m,2H); 3,35–3,50 (m,2H); 3,21 (d, J=6 Hz, 2H); 2,25 (s,3H). |
| 14 | 7,18–7,52 (m,1H); 6,40–6,70 (m,2H); 5,95 (dt, J$_1$=7 Hz, J$_2$=12 Hz, 1H); 5,50–5,75 (m,2H); 4,80–4,93 (m,2H); 3,14–3,33 (m,4H); 2,22 (s,3H); 1,23 (s,9H). |
| 15 | 7,18–7,55 (m,7H); 6,44–6,72 (m,2H); 6,25 (dt, J$_1$=7 Hz, J$_2$=17 Hz, 1H); 5,60–5,76 (m,1H); 4,70–4,84 (m,2H); 3,10–3,30 (m,4H); 2,24 (s,3H). |
| 16 | 7,30–7,55 (m,1H); 6,43–6,74 (m,2H); 6,10 (dt, J$_1$=7 Hz, J$_2$=18 Hz, 1H); 5,50–5,75 (m,2H); 4,72–4,85 (m,2H); 3,15–3,25 (m,2H); 3,05 (dd, J$_1$=1,5 Hz, J$_2$=7 Hz, 2H); 2,20 (s, 3H); 1,23 (s,9H). |
| 17 | 6,68–7,30 (m,3H); 5,95 (dt, J$_1$=7 Hz, J$_2$=12 Hz, 1H); 5,73–5,87 (m,1H); 5,63 (d, J=12 Hz, 1H); 4,8–4,9 (m,2H); 3,2–3,36 (m,4H); 2,26 (s,3H); 1,27 (s,9H). |
| 18 | 6,70–7,30 (m,3H); 6,10 (dt, J$_1$=7 Hz, J$_2$=18 Hz, 1H); 5,75–5,90 (m,1H); 5,64 (d, J=18 Hz, 1H); 4,8–4,9 (m,2H); 3,18–3,28 (m,2H); 3,07 (d, J=7 Hz, 2H); 2,22 (s,3H); 1,24 (s, 9H). |
| 19 | 6,73–7,50 (m,8H); 6,59 (d, J=18 Hz, 1H); 6,27 (dt, J$_1$=7 Hz, J$_2$=18 Hz, 1H); 5,75–5,93 (m,1H); 4,8–4,95 (m,2H); 3,15–3,35 (m,4H); 2,28 (s,3H). |
| 20 | 6,73–7,50 (m,8H); 6,60 (d, J=18 Hz, 1H); 6,30 (dt, J$_1$=7 Hz, J$_2$=18 Hz, 1H); 5,76–5,92 (m,1H); 4,70–4,82 (m,2H); 3,16–3,32 (m,4H); 2,29 (s,3H). |
| 21 | 6,70–7,30 (m,3H); 6,11 (dt, J$_1$=7 Hz, J$_2$=18 Hz, 1H); 5,5–5,9 (m,2H); 4,7–4,8 (m,2H); 3,17–3,26 (m,2H); 3,06 (dd, J$_1$=1 Hz, J$_2$=7 Hz, 2H); 2,22 (s,3H); 1,26 (s,9H). |
| 22 | 6,70–7,30 (m,3H); 5,97 (dt, J$_1$=7 Hz, J$_2$=12 Hz, 1H); 5,5–5,89 (m,1H); 5,65 (d, J=12 Hz, 1H); 4,7–4,8 (m,2H); 3,2–3,35 (m,4H); 2,27 (s,3H); 1,29 (s,9H). |
| 23 | 7,2–7,48 (m,5H); 7,03 (d, J=2 Hz, 1H); 6.88 (d, J=2 Hz, 1H); 6,55 (d, J=18 Hz, 1H); 6,07–6,40 (m,2H); 4,5–4,6 (m, 2H); 3,62–3,72 (m,2H); 3,19 (d, J=7 Hz, 2H); 2,22 (s,3H). |
| 24 | 6,8–7,5 (m,8H); 6,55 (d, J=18 Hz, 1H); 6,10–6,40 (m,2H); 4,48–4,60 (m,2H); 3,62–3,76 (m,2H); 3,20 (d, J=7 Hz, 2H); 2,24 (s,3H). |
| 25 | 6,8–7,5 (m,8H); 6,60 (d, J=18 Hz, 1H); 6,28 (dt, J$_1$=7 Hz, J$_2$=18 Hz, 1H); 5,7–5,85 (m,1H); 4,74–4,88 (m,2H); 3,1–3,35 (m,4H); 2,26 (s,3H); |
| 26 | 6.70–7,50 (m,4H); 5,96 (dt, J$_1$=7 Hz, J$_2$=12 Hz, 1H); 5,52–5,70 (m,2H); 3,20–3,34 (m,4H); 2,23 (s,3H); 1,40 (s,6H); 1,25 (s,9H). |
| 27 | 6,70–7,50 (m,4H); 6,11 (dt, J$_1$=7 Hz, J$_2$=18 Hz, 1H); 5,50–5,75 (m,2H); 3,21 (s, breit, 2H); 3,06 (d, J=7 Hz, 2H); 2,21 (s,3H); 1,40 (s,6H); 1,23 (s,9H). |
| 28 | 6,77–7,6 (m,9H); 6,61 (d, J=18 Hz, 1H); 6,34 (dt, J$_1$=7 Hz, J$_2$=18 Hz, 1H); 5,64 (s,1H); 3,32 (s,2H); 3,25 (d, J=7 Hz, 2H); 2,31 (s,3H); 1,46 (s,6H). |
| 29 | 6,85–7,68 (m,9H); 6,46 (d, J=18 Hz, 1H); 6,24 (dt, J$_1$=7 Hz, J$_2$=18 Hz, 1H); 5,92–6,13 (m,1H); 3,25–3,40 (m,4H); 3,18 (d, J=7 Hz, 2H); 2,23 (s,3H). |

The required starting materials can be prepared for example as follows.

(A) N-(6,6-dimethylhept-2-en-4-ynyl)-methylamine (for compounds 3, 8, 10–12, 14, 16–18, 21, 22, 26 and 27)

(a) 172 ml of a 20% solution of n-butyllithium in hexane are added dropwise under an inert gas atmosphere at −20° to 38 ml of 3,3-dimethyl-but-1-yne in absolute tetrahydrofuran. The mixture is then cooled to −75° and 19.3 g arcolein in 20 ml tetrahydrofuran added dropwise. The reaction mixture is then warmed to room temperature, washed with saturated aqueous NH$_4$Cl and repeatedly extracted with ether. The organic phase is separated, dried, concentrated on a rotary evaporator and distilled under vacuum, b.p. 70°–72°/1600 pascal.

(b) 1-Bromo-6,6-dimethyl-2-hepten-4-yne 50 ml 48% HBr and 10 g PBr$_3$ are stirred to homogeneity at 40°. An alcoholic solution of 13.5 g of 6,6-dimethyl-hept-1-en-4-yn-3-ol is then added dropwise at 10° and the resulting mixture stirred at room temperature for 1½ hours. The reaction mixture is poured onto ice-water and repeatedly extracted with hexane. The organic phase is separated, washed repeatedly with aqueous NaCl, dried and concentrated on a rotary evaporator. NMR spectroscopy reveals that the resulting oily reaction product comprises a 3:1 mixture of trans- and cis-1-bromo-6,6-dimethyl-hept-2-en-4-yne which is employed directly in further alkylation.

NMR: δ=5.5–6.4 (m, 2 olef. H); [4.15 (d, J=8 Hz) and 3.95 (d, J=8 Hz) ratio 1:3, 2H, =CH—CH$_2$Br]; 1.20 (m, 9H).

(c) N-(6,6-dimethylhept-2-en-4-ynyl)-methylamine 24.3 g of 1-bromo-6,6-dimethylhept-2-en-4-yne in 750 ml of ethanol are added at −50° to 245 ml of a 33% ethanolic solution of methylamine and the mixture stirred in a closed vessel at 55° for 3 hours. The resulting mixture is concentrated in a rotary evaporator and the residue taken up with chloroform and washed with 1 N NaOH and saturated NaCl. After drying over MgSO$_4$ the crude product is purified by chromatography on kieselgel (eluant toluene/ethylacetate; 4/1). A colourless oil is obtained (trans- and cis compound in ratio 3:1).

H-NMR (CDCl$_3$): δ=5.3–6.3 (m, 2H); 3.4(d)+3.16 (d, J=6 Hz) (Intensity ratio 1:3, total 2H, J=6 Hz); 2.38 (s,3H); 1.46 (s, 1H); 1.21 (s, 9H).

(b) 8-Formyl-2H-1-benzopyrane (for Example 3)

(a) o-Bromophenylpropargyl ether

A mixture of 17.3 g of o-bromophenol, 11.3 g of propargylbromide, 50 ml of acetone and 16.6 g of K$_2$CO$_3$ is refluxed for 1½ hours. After cooling the mixture is filtered, the filtrate concentrated by evaporation and the residue taken up in ethyl acetate/water. The organic phase is separated, washed with 0.5 N NaOH and water, dried over MgSO$_4$ and concentrated by evaporation. The resulting product is employed directly in the next phase.

(b) 8-Bromo-2H-1-benzopyrane

A mixture of 9.1 g crude o-bromophenylpropargyl ether and 50 ml of diethylaniline is refluxed for 7 hours in an inert gas atmosphere (bath temperature 230°). After cooling the mixture is poured onto ice-water, acidified with semi-concentrated H$_2$SO$_4$ and extracted with ethyl acetate. The organic phase is washed with 2 N HCl, aqueous NaHCO$_3$ and water, dried over MgSO$_4$ and concentrated by evaporation. The resulting crude product is purified by chromatography on kieselgel (eluant cyclohexane/toluene; 5/1).

H-NMR (CDCl$_3$): δ=7.21 (dd, J$_1$=7 Hz, J$_2$=2 Hz, 1H); 6.46–7.0 (m, 2H); 6.28 (d, J=9 Hz, 1H); 5.66 (dt, J$_1$=9 Hz, J$_2$=3.5 Hz, 1H); 4.7–5.0 (m, 2H).

(c) 8-Formyl-2H-1-benzopyrane 11 ml of a 1.6 N solution of butyllithium in hexane are added dropwise at −20° and under an inert gas atmosphere to 3.4 g of 8-bromo-2H-1-benzoprane in 70 ml of diethylether. The mixture is allowed to reach room temperature, stirred for 1.5 hours, and then 1.3 g N,N-dimethylformaide dissolved in 10 ml diethyl ether added dropwise, the temperature being kept at 10°-25° by cooling with ice-water. The reaction proceeds for 1 hour at room temperature whereupon the mixture is poured onto aqueous $NH_4Cl$ and the ether phase separated. The aqueous phase is washed twice with ether and the combined ether solutions washed with aqueous $NH_4Cl$ and water, dried over $MgSO_4$ and concentrated by evaporation. The crude product is purified by chromatography on kieselgel (eluant toluene/ethyl acetate; 15/1).

H-NMR (CDCl$_3$): $\delta = 10.3$ (s,1H); 7.58 (dd, $J_1 = 7$ Hz, $J_2 = 2$ Hz, 1H); 6.65-7.23 (m, 2H); 6.40 (d, J = 10 Hz, 1H); 5.76 (dt, $J_1 = 10$ Hz, $J_2 = 3.5$ Hz, 1H); 4.8-5.0 (m, 2H).

(C) 4-Formyl-2H-1-benzothiopyrane (for Example 29)

(a) 4-Cyano-2H-1-benzothiopyrane 80 mg of zinc iodide are added to 1.7 g 1-thiochroman-4-one in benzene followed by, dropwise, with stirring at room temperature, 2.4 g of trimethylsilylcyanide. After 8 hours reaction 2.8 ml of POCl$_3$ and 16 ml of pyridine are added and the mixture refluxed for 8 hours. After cooling the mixture is poured onto ice/-conc. HCl and, after addition of dichloromethane, separated. The organic phase is dried over MgSO$_4$, concentrated by evaporation and purified by chromatography on kieselgel (eluant hexane/ethyl acetate; 4/1).

H-NMR(CDCl$_3$): $\delta = 6.9$-7.6 (m, 4H); 6.64 (t, J=5.5 Hz, 1H); 3.45 (d, J=5.5 Hz, 2H).

(b) 4-Formyl-2H-1-benzothiopyrane 0.5 g of 4-cyano-2H-1-benzothiopyrane in 2 ml of benzene are reacted with 2 ml of a 20% solution of diisobutylaluminium hydride in toluene and the mixture stirred for 4 hours at room temperature. The resulting mixture is poured onto 20% H$_2$SO$_4$ and the organic phase separated, washed with saturated aqueous NaCl and dried over MgSO$_4$. After concentration by evaporation the product is purified by chromatography over kieselgel (eluant hexane/ethyl acetate).

H-NMR (CDCl$_3$): $\delta = 9.44$ (s, 1H); 7.77-8.08 (m, 1H); 6.93-7.30 (m,3H); 6.77 (t, J=6 Hz, 1H); 3.44 (d, J=6 Hz, 2H).

(D) 7-Fluoro-4-chloromethyl-2H-1-benzopyrane (for Examples 14 to 16)

1.22 g of pyridine are added to 28 g of 7-fluoro-4-hydroxymethyl-2H-1-benzopyrane in 50 ml of diethylether. The mixture is cooled to 5° and 2 g of thionylchloride in 10 ml diethylether slowly added dropwise. The reaction is continued for 30 minutes at 5°-10° and 2 hours at room temperature. The resulting mixture is poured onto ice-water, the organic phase separated and the aqueous phase extracted with a further 20 ml of diethyl ether. The combined ether solutions are dried over MgSO$_4$ and concentrated by evaporation.

H-NMR(CDCl$_3$): $\delta = 7.0$-7.32 (m,1H); 6.22-6.85 (m,2H); 5.82 (t, J=3.5 Hz, 1H); 4.80 (d, J=3.5 Hz, 2H); 4.33 (s, 2H).

Other intermediates of formula IIIa can be obtained analogously.

(E) N-(6-Chloro-2H-1-benzopyrane-4yl-methyl)methylamine (for Examples 1, 5, 8 and 9)

500 ml of 33% ethanolic methylamine are added dropwise under ice-water cooling to 105 g 6-chloro-4-chloromethyl-2H-1-benzopyrane. Reaction is continued for 8 hours at room temperature, the mixture concentrated by evaporation and the residue taken up in dichloromethane. The mixture is washed with 500 ml each of 1 N NaOH and water, dried over MgSO$_4$ and concentrated by evaporation. Distillation of the residue yields the title product b.p. 116°-120°/13.3 pascal.

NMR(CDCl$_3$): $\delta = 6.55$-7.30 (m, 3H); 5.6-5.9 (m, 1H); 4.62-4.86 (m, 2H); 3.5 (d, J=1.5 Hz, 1H); 2.5 (s, 3H); 1.23 (s, 1H).

Other intermediates of formula III can be obtained analogously.

(F) Trans,trans-6,6-dimethylhept-2,4-dien-1-ol (for Example 1)

(a) 6,6-Dimethyl-2,4-heptadienal

Freshly distilled 4-methoxy-but-3-en-1-yne is added dropwise under cooling to a solution of t-butyl-magnesium bromide in absolute tetrahydrofuran and the mixture stirred for 45 minutes at room temperature. The reaction mixture is first mixed with 13.6 g of ethanol, then, under cooling and inert gas atmosphere, reacted with 5.9 g of LiAlH$_4$ and stirred overnight at room temperature. It is then mixed with saturated aqueous NH$_4$Cl under cooling, acidified with H$_2$SO$_4$ and extracted with ether. The pure product is obtained by vacuum distillation b.p. (bulb tube) 50°/0.26 mbar.

(b) Trans,trans-6,6-dimethyl-2,4-heptadien-1-ol 2 g Trans,trans-6,6-dimethyl-2,4-heptadienal are dissolved in ethanol and reacted at room temperature with 275 mg NaBH$_4$ in successive portions. After stirring for ca. 1 hour at room temperature the mixture is concentrated on a rotary evaporator, the residue partitioned between ethyl acetate and saturated aqueous NaHCO$_3$ and the organic phase dried and concentrated under vacuum. The oily crude product is further reacted directly.

NMR: $\delta = 5.6$-6.4 (m, 4 olef. H); 4.2 (d, J=6 Hz, 2H); 1.6 (br, OH); 1.04 (s,9H).

(G) 4-Bromomethyl-2,2-dimethyl-2H-1-benzopyrane (and 3-bromo-2,2-dimethyl-3,4-dihydro-4-methylen-1-benzopyrane) (for Examples 26-28)

0.5 g of 2,2,4-trimethyl-2H-1-benzopyrane in 10 ml of carbontetrachloride are reacted with 0.5 g of N-bromosuccinimide and the mixture refluxed for 1 hour, filtered and concentrated by evaporation. A 1:2 mixture of products is obtained which can be used directly for the alkylation of a secondary amine.

FORMULA SHEET

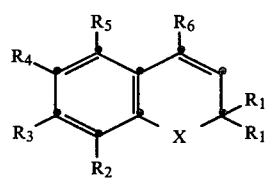

I 4,382,951
-continued
FORMULA SHEET
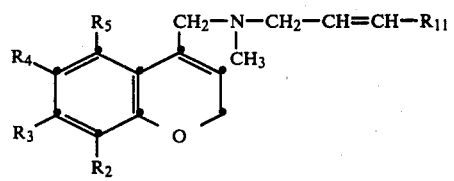 I'
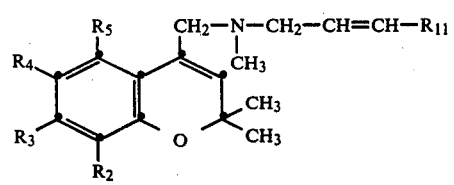 I''
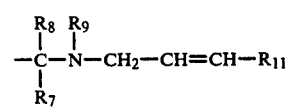 II
 IIa
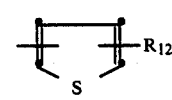 IIb
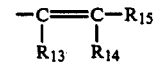 IIc
 IId
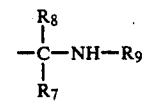 IIe
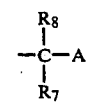 IIf
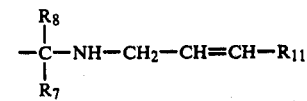 IIg
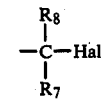 IIh
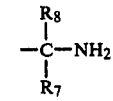 IIi
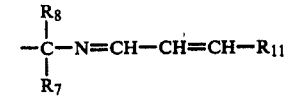 IIj
-continued
FORMULA SHEET
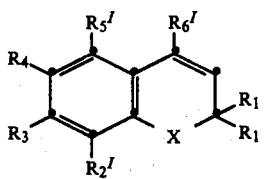 III
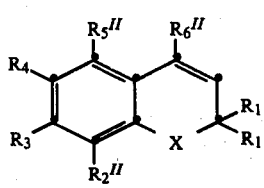 IIIa
$A-CH_2-CH=CH-R_{11}$  IV
$R_9-NH-CH_2-CH=CH-R_{11}$  IVa
$A-CH_2-CH=CH-C\equiv C-R_{16}$  IVb
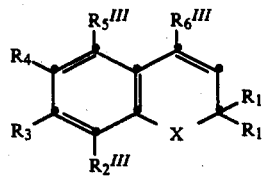 V
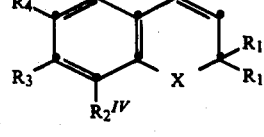 VI
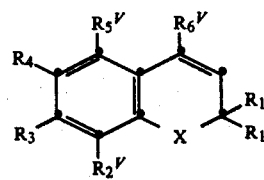 VIII
$R_9-NH_2$  IX
$H\equiv C-R_{16}$  X
 XV
$O=CH-CH=CH-R_{11}$  XVI
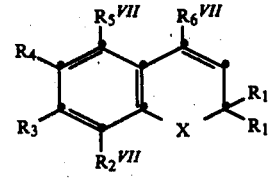 XVII

Reaction Scheme 1

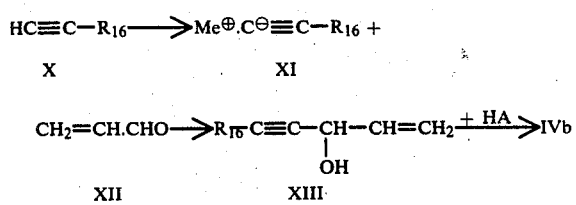

Reaction Scheme 2

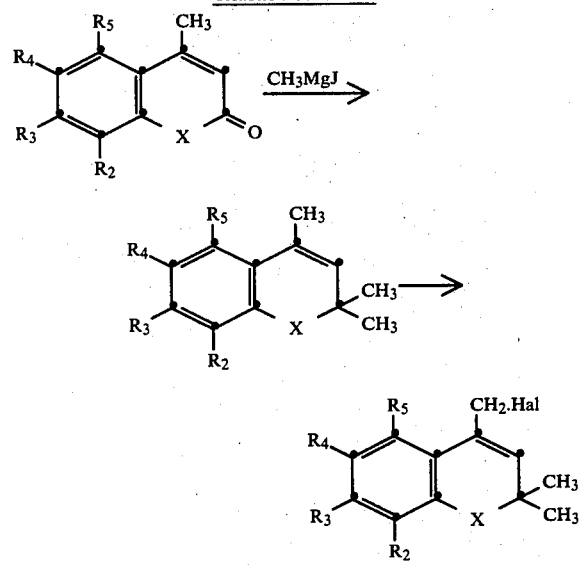

We claim:

1. A compound of formula I:

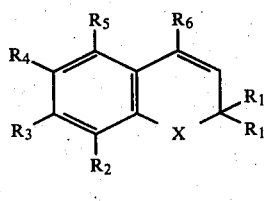

wherein
X represents oxygen or sulphur,
each $R_1$ represents independently hydrogen or methyl,
$R_3$ and $R_4$ represent independently hydrogen, halogen, lower alkyl or lower alkoxy,
$R_2$ and $R_5$ represent independently hydrogen, halogen, lower alkyl, lower alkoxy or a group of formula II:

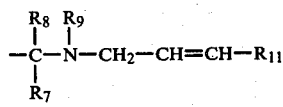

wherein
$R_7$ and $R_8$ represent independently hydrogen or lower alkyl,
$R_9$ represents lower alkyl and
$R_{11}$ represents a group of formula IIa, IIb, IIc or IId,

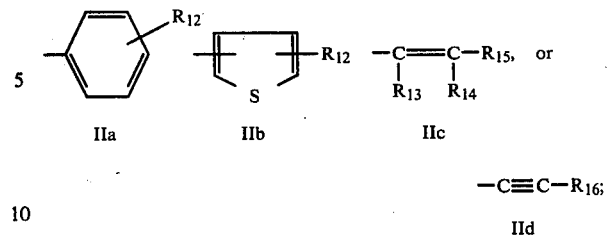

wherein
$R_{12}$ represents hydrogen, halogen, trifluoromethyl, lower alkyl or lower alkoxy,
at least one of $R_{13}$, $R_{14}$ and $R_{15}$ represents alkyl and the others represent hydrogen or alkyl, or $R_{14}$ together with either $R_{13}$ or $R_{15}$ forms a $C_{3-6}$ methylene bridge and
$R_{16}$ represents lower alkyl, lower alkenyl or α-hydroxy lower alkyl; and
$R_6$ represents hydrogen, lower alkyl or a group of formula II, whereby one and only one group of formula II is always present as $R_2$, $R_5$ or $R_6$;

or an acid addition salt thereof.

2. A compound according to claim 1 wherein any "lower alkyl" or "lower alkoxy" radical has 1 to 4 carbon atoms, any "alkyl" radical has 1 to 10 carbon atoms, any "lower alkenyl" radical has 3 to 6 carbon atoms and any halogen is fluorine, chlorine or bromine.

3. A compound according to claim 2, wherein any "lower alkyl" or "lower alkoxy" radical has 1 or 2 carbon atoms, any "alkyl" radical contains 1 to 5 carbon atoms and any "lower alkenyl" radical contains 3 or 4 carbon atoms.

4. A compound according to claim 3 wherein the $R_1$'s are identical and are hydrogen or methyl,
$R_2$ and $R_5$, independently, are hydrogen or halogen,
$R_3$ and $R_4$, independently, are hydrogen, halogen or lower alkyl,
$R_6$ is a group of formula II,
$R_7$ and $R_8$ are hydrogen,
$R_9$ is methyl,
$R_{12}$, $R_{13}$ and $R_{14}$ are hydrogen,
$R_{15}$ and $R_{16}$ are lower alkyl and
X is oxygen.

5. A compound according to claim 4 wherein $R_{11}$ is a radical of formula IId.

6. A compound according to claim 4 wherein the double bond between $R_{11}$ and the nitrogen atom is in the trans configuration.

7. A compound according to claim 1 of the formula

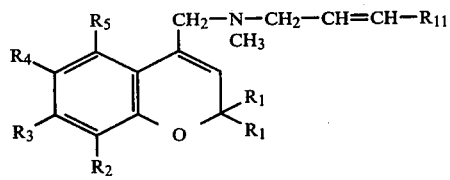

wherein the $R_1$'s are the same and are hydrogen or methyl.

8. A compound according to claim 1 which is trans-N-(6-fluoro-2H-1-benzopyran-4-yl-methyl)-N-methyl-6,6-dimethylhept-2-en-4-ynyl-1-amine or its hydrochloride.

9. A compound according to claim 1 which is trans-N-(2H-1-benzopyran-4-yl-methyl)-N-methyl-6,6-dimthylhept-2-en-4-ynyl-1-amine or its hydrochloride.

10. A chemotherapeutic composition comprising a chemotherapeutically effective amount of a compound of formula I as claimed in claim 1 or a chemotherapeutically acceptable acid addition salt thereof together with a chemotherapeutically acceptable diluent or carrier.

11. A composition according to claim 10 wherein the chemotherapeutically effective amount is an anti-mycotic-effective amount.

12. A chemotherapeutic composition comprising a chemotherapeutically effective amount of a compound of formula I as defined in claim 3 or a chemotherapeutically acceptable acid addition salt thereof together with a chemotherapeutically acceptable diluent or carrier.

13. A composition according to claim 12 wherein the acid addition salt is a hydrochloride, a hydrogen fumarate or a naphthalene-1,5-disulphonate.

14. A method of treating diseases or infections caused by mycetes which comprises administering to a subject in need of such treatment an effective amount of a compound of formula I as claimed in claim 1 or a chemotherapeutically acceptable acid addition salt thereof.

15. A method of chemotherapeutically treating a subject in need of such treatment which comprises administering to said subject a chemotherapeutically effective amount of a compound of formula I as claimed in claim 1 or a chemotherapeutically acceptable acid addition salt thereof.

16. A method of treating diseases or infections caused by mycetes which comprises administering to a subject in need of such treatment an anti-mycotic-effective amount of a compound of formula I as claimed in claim 4 or a chemotherapeutically acceptable acid addition salt thereof.

17. A method according to claim 14 wherein the compound of formula I or its salt is administered in a daily amount of about 4 to 30 mg per kg of bodyweight of the subject.

18. A method according to claim 17 wherein the total daily dosage is about 300 to 2,000 mg.

19. A method according to claim 16 wherein the acid addition salt is a hydrochloride, a hydrogen fumarate or a naphthalene-1,5-disulphonate.

* * * * *